United States Patent [19]

Bouisset et al.

[11] Patent Number: 5,189,170

[45] Date of Patent: Feb. 23, 1993

[54] PROCESS FOR THE PREPARATION OF PHENYLACETIC DERIVATIVES OF THIENO-PYRIDINES

[75] Inventors: Michel Bouisset, Sisteron; Joël Radisson, Toulouse, both of France

[73] Assignee: Sanofi, Paris, France

[21] Appl. No.: 677,482

[22] Filed: Mar. 29, 1991

Related U.S. Application Data

[62] Division of Ser. No. 540,483, Jun. 19, 1990, Pat. No. 5,036,156.

[30] Foreign Application Priority Data

Sep. 29, 1989 [FR] France ................ 89 12787

[51] Int. Cl.$^5$ ............................................. C07D 495/04
[52] U.S. Cl. ...................................................... 546/114
[58] Field of Search ................ 546/114; 562/422, 496; 568/812

[56] References Cited

U.S. PATENT DOCUMENTS 4,529,596 7/1985 Aubert et al. .............. 546/114
5,036,156 7/1991 Bouisset et al. ............. 562/496

FOREIGN PATENT DOCUMENTS 2597102 10/1987 France .................. 546/114

*Primary Examiner*—Bernard Dentz
*Attorney, Agent, or Firm*—Wegner, Cantor, Mueller & Player

[57] ABSTRACT

Compounds of formula:

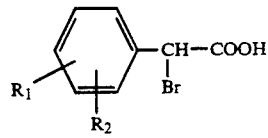

in which $R_1$ and $R_2$ are hydrogen or halogen, are prepared by reacting an aldehyde of formula:

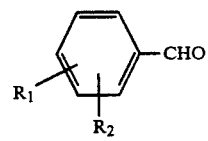

with CHBr$_3$ and KOH in a mixture of an inert solvent and water. Further an ester of compound (I) wherein $R_1$ is H and $R_2$ is 2-Cl is reacted with 4,5,6,7-tetrahydrothieno[3,2-c]pyridine to produce a compound of formula III:

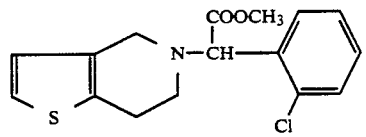

which is useful as a medicament.

5 Claims, No Drawings

PROCESS FOR THE PREPARATION OF PHENYLACETIC DERIVATIVES OF THIENO-PYRIDINES

This application is a divisional of Ser. No. 07/540,483, filed Jun. 19, 1990 now U.S. Pat. No. 5,036,156.

The present invention relates to a process for the preparation of thieno[3,2-c] pyridine derivatives, including clopidogrel, and of intermediates in their synthesis, the α-bromo-phenylacetic acids of formula:

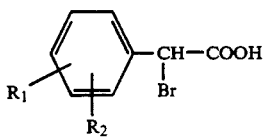

in which $R_1$ and $R_2$, identical or different, each denotes hydrogen or halogen. These acids are known products, used as intermediates in the synthesis of various compounds, in particular in the pharmaceutical and agrochemical industries, optionally after esterification.

Thus, α-bromo-phenylacetic acid is used, for example, in the preparation of the semi-synthetic penicillins described in patent DE-A-2 624 064, of anti-ulcer thiazolium salts described in U.S. Pat. No. 4,289,697, of thiazolo[2,3-b] thiazolium salts, inhibitors of metastases, described in U.S. Pat. No. 4,327,221, and also of thieno[3,2-c] pyridine derivatives, described in EP-A-99802, of formula II

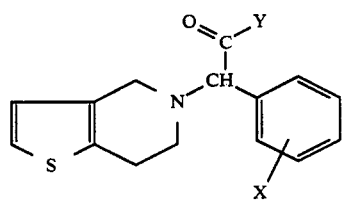

in which Y may represent hydroxyl OH or the OR group in which R is a straight or branched lower alkyl radical, or Y denotes a N $R_1$ $R_2$ group in which $R_1$ and $R_2$ are independently hydrogen or a straight or branched lower alkyl group, or $R_1$ and $R_2$ form together with the nitrogen atom to which they are attached a pyrrolidino, morpholino, piperidino or 4-benzyl piperazino group, and X denotes hydrogen, halogen or a lower alkyl radical.

Up to now, the compounds of formula I have been prepared either from the corresponding phenylacetic acids by reaction with N-bromosuccinimide or bromine, or from the mandelic acids by reaction with a concentrated aqueous solution of hydrobromic acid. The phenylacetic acids are themselves prepared in several steps from toluene, through the intermediary of phenylacetonitrile, whereas the mandelic acids can be prepared from benzaldehydes, which are reacted with either an alkali cyanide in a Strecker reaction in order to form the mandelonitrile which is then hydrolysed in aqueous medium, or with bromoform in the presence of potassium hydroxide.

These preparation processes which involve the utilization of expensive or dangerous reagents give low yields, and it was desirable to find a new process which makes it possible to prepare economically in particular the platelet aggregation inhibiting compound of formula III:

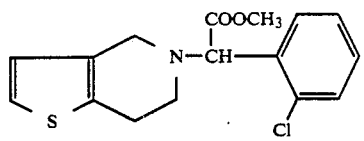

the preparation of which by the action of methyl alpha-chloro (2-chloro) phenylacetate on tetrahydrothieno [3,2-c] pyridine is known to give moderate yields; in fact, it became apparent during initial experiments that the replacement of the alpha-chlorinated derivative by a pure alpha-brominated derivate increases the yield of the reaction at the heterocyclic nitrogen leading to the compound III.

The invention enables the compounds of formula I to be prepared in a single step with good yields from the corresponding benzaldehydes, by using commercial reagents which can be handled without requiring specific precautions.

According to one of its aspects, the invention relates to a process for the preparation of alpha-bromophenylacetic acids which consists of reacting a benzaldehyde of formula:

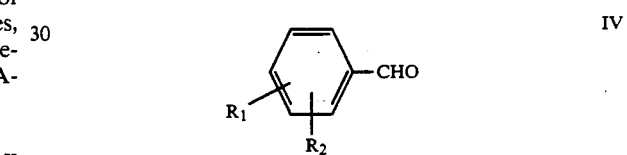

in which $R_1$ and $R_2$ have the same meaning as before, with tribromomethane and potassium hydroxide in water and in the presence of an inert solvent.

The solvent may be a solvent miscible with water, in particular an ether such as dioxane, 1,2-dimethoxy ethane, dimethoxymethane; the reaction medium is then constituted preferably of a mixture of solvent and water at about 50% by volumes, but water may be added during the course of the reaction to give a medium containing up to 90% water.

The solvent may also be a solvent immiscible with water such as an aromatic hydrocarbon, in particular benzene or toluene, or an ether, such as isopropyl ether. With these solvents, the reaction must be carried out in the presence of a phase transfer catalyst, such as a quaternary ammonium salt, in particular a tetrabutylammonium or benzyltrimethylammonium halide, or a phosphonium salt.

It is preferable to react the aldehyde and bromoform in approximately equivalent amounts, namely from 0.8 to 1.2 equivalent(s) of $CHBr_3$, in the presence of 3 to 4 equivalents of potassium hydroxide. The KOH concentration in the aqueous medium is usually from 10 g to 50 g per 100 ml.

In order to limit side reactions and in particular the formation of mandelic acid, the reaction is carried out at a quite low temperature, usually between −5° C. and +10° C., and preferably between 0° C. and 5° C. Depending on the temperature, the reaction mixture is stirred from several hours to a few days.

When the reaction is carried out in homogeneous medium, the aqueous phase is washed at the end of the reaction by an immiscible solvent such as isopropyl ether or dichloromethane in order to remove the impurities before acidifying and extracting the final product into a solvent immiscible with water, according to a standard procedure. The mandelic acid which may have formed is separated from the alphabrominated derivative, by using, for example, the difference in their distribution coefficients between toluene and water.

The procedure is quite especially suitable for the preparation of compounds of formula I in which $R_1=H$ and $R_2=Cl$, Br or F; the yields of pure products are usually higher than 50% and frequently more than 70%. On the other hand, it has been observed that it gives only very low yields when the aromatic nucleus is substituted by alkyl or alkoxy groups. Moreover, it is not possible to replace bromoform by chloroform in order to prepare the corresponding alpha-chlorinated acids under the same conditions.

Another object of the invention is a process for the preparation of the compound of formula III and its pharmaceutically acceptable salts, which consists of reacting an ester of alpha-bromo (2-chloro) phenylacetic acid with 4,5,6,7-tetrahydro thieno[3,2-c] pyridine in the presence of at least one equivalent of a base in a polar solvent commonly used for this type of substitution such as an alcohol, such as methanol or ethanol, a ketone, such as acetone or methylethylketone, an ester, such as ethyl acetate, an ether, such as tetrahydrofuran, or isopropyl ether, acetonitrile, dimethylformamide. As base, it is preferable to use an alkali carbonate such as $K_2CO_3$, $NaHCO_3$ or $Na_2CO_3$. At the end of the reaction, the solids are filtered off and the solvent is evaporated under reduced pressure. The hydrochloride of the final product may then be prepared by reaction of a concentrated aqueous solution of hydrochloric acid on the amino compound in solution in ethyl acetate. It is also possible to react the brominated acid with the nitrogen heterocycle and then esterifying the product obtained but it is preferable to prepare the alpha-brominated ester beforehand, for example by the action of the alcohol on the brominated acid in the presence of a strong acid.

When it is required to prepare clopidogrel (international non-proprietary name), i.e. the dextro-rotatary stereoisomer of the compound of formula III, the recrystallization of salts of the racemic amine with an optically active acid, such as camphosulfonic acid, is subsequently carried out as mentioned in EP-A-0281459.

In what follows, examples for carrying out the invention are described. The products obtained are analytically pure and their physico-chemical values are identical with those mentioned in the literature.

EXAMPLE 1

α-bromo (2-chloro) phenylacetic acid

A solution of 100 g of (2-chloro)benzaldehyde and 198 g of tribromomethane in 60 ml of dioxane is introduced into a vigorously stirred mixture of 160 g of ice, 160 g of potassium hydroxide and 100 ml of dioxane at a temperature of about 0° C.

After one hour, 1 liter of water is introduced and the reaction mixture is stirred for 18 hours at a temperature between 0° C. and 5° C. It is then washed 3 times with 400 ml of cold isopropyl ether. The aqueous phase is acidified by the addition of a concentrated aqueous solution of hydrochloric acid before two extractions are made with 400 ml of toluene. The final product is isolated from the toluene phase after drying and evaporation of the solvent. After recrystallization from toluene, 111 g of acid are isolated. Yield 63% based on the aldehyde.

EXAMPLES 2 TO 6

The compounds listed in Table I are prepared by application of the same method.

TABLE 1

| EXAMPLE | $R_1$ | $R_2$ | YIELD |
|---|---|---|---|
| 2 | H | H | 51% |
| 3 | H | Cl-4 | 74% |
| 4 | H | Br-2 | 71% |
| 5 | H | F-2 | 65% |
| 6 | Cl-2 | Cl-4 | 68% |

EXAMPLE 7

α-bromo(2-chloro)phenylacetic acid

A solution of 70.5 g of (2-chloro)benzaldehyde and 127 g of tribromomethane in 150 ml of isopropyl ether is added to a vigorously stirred solution of 135 g of KOH and 12.5 g of benzyltrimethylammonium chloride in 400 ml of water at a temperature lower than 0° C.

The mixture is stirred for 26 hours at a temperature between −5° C. and 0° C. 400 ml of water and 250 ml of isopropyl ether are then added and the organic phase is separated. After the aqueous phase has been washed with 300 ml of isopropyl ether, it is acidified by the addition of concentrated sulfuric acid and the final product is recovered by two extractions with 400 ml of isopropyl ether. The organic solvent is then evaporated from the extracts and the residue dissolved in 300 ml of toluene; the toluene phase is washed twice with 60 ml of water, then concentrated in a vacuum to 60 ml. The final product precipitates slowly from this mixture.

In this way 58.5 g of the desired acid are isolated-yield 47%.

EXAMPLE 8

α-bromo (2-chloro)phenylacetic acid

A solution of 141 g of (2-chloro) benzaldehyde and 270 g of tribromomethane in 500 ml of ethyl ether is added to a solution of 270 g of potassium hydroxide and 34 g of tetrabutylphosphonium bromide in 800 ml of water. The mixture is stirred for 24 hours at 0° C.

After work-up as in example 2, 119 g of acid are obtained-yield 48%.

EXAMPLE 9

α-bromo (2-chloro) phenylacetic acid

A solution of 70.3 g of (2-chloro) benzaldehyde and 139 g of tribromomethane diluted in 50 ml of 1,2-dimethoxy ethane are added to a vigorously stirred mixture of 131 ml of water, 114 g of potassium hydroxide (titer 86%) and 50 ml of 1,2-dimethoxy ethane at a temperature of about −5° C. After 3 hours at about −5° C., 500 ml of water are added to the reaction mixture at a temperature lower than or equal to 0° C., then the temperature is allowed to rise to 10° C. and maintained there for 10 hours.

The reaction mixture is then extracted four times with 95 ml of dichloromethane. The aqueous phase remaining is then acidified by the addition of concentrated hydrochloric acid, then extracted twice with 100 ml of isopropyl ether. After drying, evaporating the solvent and recrystallizing from toluene, 84.6 g of the pure expected acid are recovered-yield 67%.

A second crop may be isolated from the toluene solution which amounts to a further 14.5 g of acid.

EXAMPLE 10 methyl α-(4,5,6,7-tetrahydro thieno [3,2-c] 5-pyridyl) 2-chlorophenyl acetate.

a) 55 g of α-bromo (2-chloro) phenyl acetic acid obtained in example 1 were dissolved in 200 ml of methanol; 30 g of concentrated sulfuric acid are then added and the mixture is refluxed for 4 hours. The solvent is then removed under reduced pressure, and 100 ml of isopropyl ether and 100 ml of water are added to the residue; after neutralization, the ethereal phase is dried, concentrated and the methyl ester is distilled under reduced pressure to give 53.5 g of product which are used as such in the next step.

b) 7 g of pure 4,5,6,7-tetrahydro thieno[3,2-c] pyridine are added to 13.5 g of methyl α-bromo 2-chloro phenylacetate in 80 ml of methanol, and 6 g of sodium bicarbonate. The mixture is stirred for 6 hours at 80° C., then the solids are removed by filtration and the solvent is evaporated under reduced pressure. 120 ml of ethyl acetate and 60 ml of water are then added. The organic phase is decanted off washed with water, then cooled to −10° C. A mixture of 20 g of ice and 10 ml of concentrated hydrochloric acid is then added. The precipitate which forms is isolated by filtration and dried to give 15.8 g of the hydrochloride of the expected product which melts at 130° C.

We claim:

1. A process for the preparation of a compound of formula III:

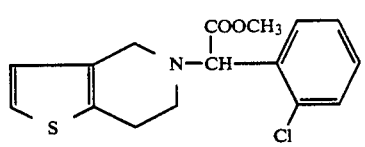

III wherein an ester of alpha-bromo (2-chloro)phenylacetic acid is reacted with 4,5,6,7-tetrahydro thieno [3,2-c] pyridine in the presence of at least one equivalent of a base in a polar solvent, wherein the alpha-bromo(2-chloro)phenylacetic acid used as the precursor of said ester is prepared by a process wherein an aldehyde of the formula:

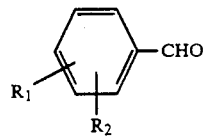

IV in which $R_1$ is H and $R_2$ is 2-Cl, is reacted with $CHBr_3$ and KOH in a mixture of an inert solvent and water.

2. The process of claim 1, wherein the alpha-bromo(2-chloro)phenylacetic acid used is prepared by a process wherein an aldehyde of the formula:

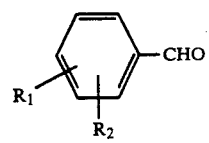

IV in which $R_1$ is H and $R_2$ is 2-Cl, is reacted with $CHBr_3$ and KOH in a mixture of an inert solvent and water at a temperature between −5° C. and 10° C.

3. The process of claim 1, wherein the alpha-bromo(2-chloro)phenylacetic acid used is prepared by a process wherein an aldehyde of formula:

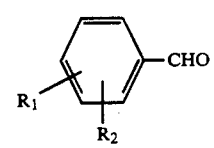

IV in which $R_1$ is H and $R_2$ is 2-Cl, is reacted with $CHBr_3$ and KOH in a mixture of an inert solvent that is immiscible in water and water in the presence of a phase transfer catalyst.

4. The process of claim 1, wherein the alpha-bromo(2-chloro)phenylacetic acid used is prepared with a solvent that is immiscible with water and in the presence of a phase transfer catalyst.

5. The process of claim 1, wherein the alpha-bromo(2-chloro)phenylacetic acid used is prepared by a process wherein an aldehyde of formula:

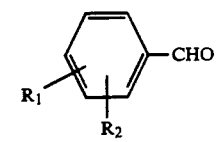

IV in which $R_1$ is H and $R_2$ is 2-Cl, is reacted with $CHBr_3$ and KOH in a mixture of an ether solvent miscible with water and water.

* * * * *